US005827198A

United States Patent [19]

Kassal

[11] Patent Number: 5,827,198

[45] Date of Patent: Oct. 27, 1998

[54] LOW-COST, DISPOSABLE, POLYMER-BASED, DIFFERENTIAL OUTPUT FLEXURE SENSOR AND METHOD OF FABRICATING SAME

[75] Inventor: James J. Kassal, East Lyme, Conn.

[73] Assignee: Flowscan, Inc., Mill Valley, Calif.

[21] Appl. No.: 754,761

[22] Filed: Nov. 21, 1996

[51] Int. Cl.[6] ........ A61B 7/04

[52] U.S. Cl. ........ 600/528; 600/586; 181/131; 310/311; 310/368; 381/190

[58] Field of Search ........ 600/485–488, 600/493, 528, 586; 310/311, 331, 332, 334, 357, 364–366, 368; 181/126, 131, 132, 139, 158; 381/153, 173, 190

[56] References Cited

U.S. PATENT DOCUMENTS

| | | | |
|---|---|---|---|
| 4,054,808 | 10/1977 | Tanaka . | |
| 4,633,122 | 12/1986 | Radice | 310/339 |
| 5,140,992 | 8/1992 | Zuckerwar et al. | 600/528 |
| 5,365,937 | 11/1994 | Reeves et al. . | |
| 5,595,188 | 1/1997 | Kassal | 600/586 |

FOREIGN PATENT DOCUMENTS

| | | |
|---|---|---|
| 146273 | 6/1985 | European Pat. Off. . |
| 528279 | 2/1993 | European Pat. Off. . |
| 2507424 | 12/1982 | France . |
| 3531399 | 3/1986 | Germany . |
| 9506525 | 3/1995 | WIPO . |

*Primary Examiner*—Jeffrey R. Jastrzab
*Attorney, Agent, or Firm*—Bachman & LaPointe, P.C.

[57] ABSTRACT

The present invention relates to a low-cost, disposable, flexure sensor with an active portion which includes first and second sensor elements formed from a piezoelectric polymer material. Each of the first and second sensor elements has a first surface and an opposed second surface. A first electrically conductive area is formed on the first surface of each sensor element and is connected to a second electrically conductive area on the second surface. In a preferred embodiment of the present invention, the electrical connection is formed by a plated hole which extends through the sensor element from the first surface to the second surface. Still further, each of the first and second sensor elements has a third electrically conductive area on the first surface, which electrically conductive area is electrically isolated from the first electrically conductive area. The active portion of the sensor includes at least one layer of an elastomeric substrate material positioned between the first and second sensor elements. Still further, a layer of hydrogel is affixed to one of the first and second sensor elements and a cover or protective layer is attached to the other of the first and second sensor elements. The hydrogel layer and the polyethylene layer are notched or otherwise configured so as to accommodate a connection tab on said sensor elements. A method for fabricating the acoustic sensor is also disclosed.

20 Claims, 4 Drawing Sheets

LOW-COST, DISPOSABLE, POLYMER-BASED, DIFFERENTIAL OUTPUT FLEXURE SENSOR AND METHOD OF FABRICATING SAME

BACKGROUND OF THE INVENTION

The present invention relates to a low cost, disposable, polymer-based, differential output flexure sensor for capturing acoustic sounds and to a method of manufacturing the sensor.

Acoustic pick-up devices that have been traditionally used for capturing heart sounds have had two distinct disadvantages: (a) they have a poor signal to noise ratio in that they are sensitive to air-borne noise which requires that a special quiet room be used for procedures involving their use; and (b) they rely on acoustic transmission from body tissue, to air, then to the device which is very inefficient (not contaneous).

Commercially available contact microphones are sometimes used to capture acoustic sounds such as heart sounds because they are not as sensitive to airborne noise. However, they also are fairly heavy and therefore substantially reduce the surface vibrations that they are trying to detect.

Many of these traditional devices have an additional disadvantage in that they must be held in place. This can introduce unwanted noise from the unavoidable quivering of muscles and creaking of joints in a user's fingers. Belts could be used to avoid this but many users find them objectionable from a convenience standpoint.

A number of attempts have been made to deal with these problems. U.S. Pat. No. 5,365,937 to Reeves et al. shows one such attempt. The device shown in this patent has a diaphragm formed from a piezoelectric transducer material with metallization layers on its surfaces.

In another construction shown in published PCT application WO 95 06525, an acoustic sensor, designed to sense the flexing of a patient's skin that is a result of the localized nature of internal body sounds and generate an electrical signal analogous to the flexure of the skin, had as its principal components two thin film piezoelectric sensing portions, two layers of a compliant, substantially incompressible material, a flexible and elastic adhesive layer between respective ones of the sensing portions and the incompressible material layers, an electrical connector at one end of the sensing device, an optional neutral plane inducer, an electrostatic shield for the electrical connector, a moisture barrier/protective coating, and an optional adhesive or cream layer for adhering the sensor device to the skin of the patient. The design of this sensor was deficient however in several respects. First, the device could not be fabricated in a reliable and cost effective manner. Second, the device had an unacceptably short shelf life. Many ceased to function properly upon completion of the assembly process.

In a next generation of devices, a pad-like acoustic sensor was developed which could be feasibly manufactured. The sensor was formed from a single piece of piezoelectric material having electrically conductive areas on two spaced apart and opposed surfaces. The electrically conductive areas were electrically connected to electrical contacts or connector pins used to connect the sensor to a measuring device. This sensor is shown in pending U.S. patent application Ser. No. 08/507,570 now U.S. Pat. No. 5,595,188, for An Assembly Process For A Polymer-Based Acoustic Differential Output Sensor by James J. Kassal, which application is assigned to the assignee of the instant application.

The fabrication process described in the Kassal patent application has been used to produce over 40,000 sensors.

Although these sensors work very well and have virtually unlimited shelf life, the manufacturing cost is considered to be high for a disposable device. In addition, field trials in the emergency medical arena as well as clinical evaluations have indicated a need to modify certain performance characteristics and to improve the convenience of using the sensor.

SUMMARY OF THE INVENTION

Accordingly, it is a principal object of the present invention to provide a low-cost, disposable, polymer-based, differential-output flexure sensor.

It is a further object of the present invention to provide a sensor as above having improved performance characteristics.

It is yet a further object of the present invention to provide a sensor as above having enhanced convenience.

Still further, it is an object of the present invention to provide a low cost method of manufacturing said sensor.

The foregoing objects are attained by the sensor of the present invention and the improved method of manufacturing described herein.

In accordance with the present invention, a low-cost, disposable, acoustic sensor has an active portion which includes first and second sensor elements formed from a piezoelectric polymer material. Each of the first and second sensor elements has a first surface and an opposed second surface. A first electrically conductive area is formed on the first surface of each sensor element and is connected to a second electrically conductive area on the second surface. In a preferred embodiment of the present invention, the electrical connection is formed by a plated hole which extends through the sensor element from the first surface to the second surface. Still further, each of the first and second sensor elements has a third electrically conductive area on the first surface, which electrically conductive area covers the majority of the surface area of the first surface and is electrically insulated from the first electrically conductive area. The active portion of the acoustic sensors in accordance with the present invention further includes at least one layer of an elastomeric substrate material positioned between the first and second sensor elements.

Still further, a layer of hydrogel or medical grade adhesive is laminated to one of the first and second sensor elements and an optional cover layer, preferably formed by polyethylene material, is laminated to the other of the first and second sensor elements. The hydrogel or medical grade adhesive layer and the polyethylene layer are notched or positioned so as to accommodate a connection tab on the sensor elements containing the first electrically conductive area.

The acoustic sensors of the present invention are fabricated by providing first and second sensor elements having a substantially rectangular main portion, a connecting tab portion adjoining the main portion, a first surface with a first electrically conductive area positioned over the connecting tab portion, a second surface having a second electrically conductive area, and the second electrically conductive area covering a major portion of the surface area of the second surface and being in electrical contact with the first electrically conductive area; providing a substrate having two opposed surfaces, each of the surfaces having a pressure sensitive adhesive applied thereto; and laminating a first one of the sensor elements to a first one of the opposed surfaces and a second one of the sensor elements to a second one of the opposed surfaces to form an active sensor portion.

Other details of the present invention, as well as other objects and advantages attendant thereto, are set forth in the following description and the accompanying drawings in which like reference numerals depict like elements.

DETAILED DESCRIPTION OF THE PREFERRED EMBODIMENT(S)

Figure 1:
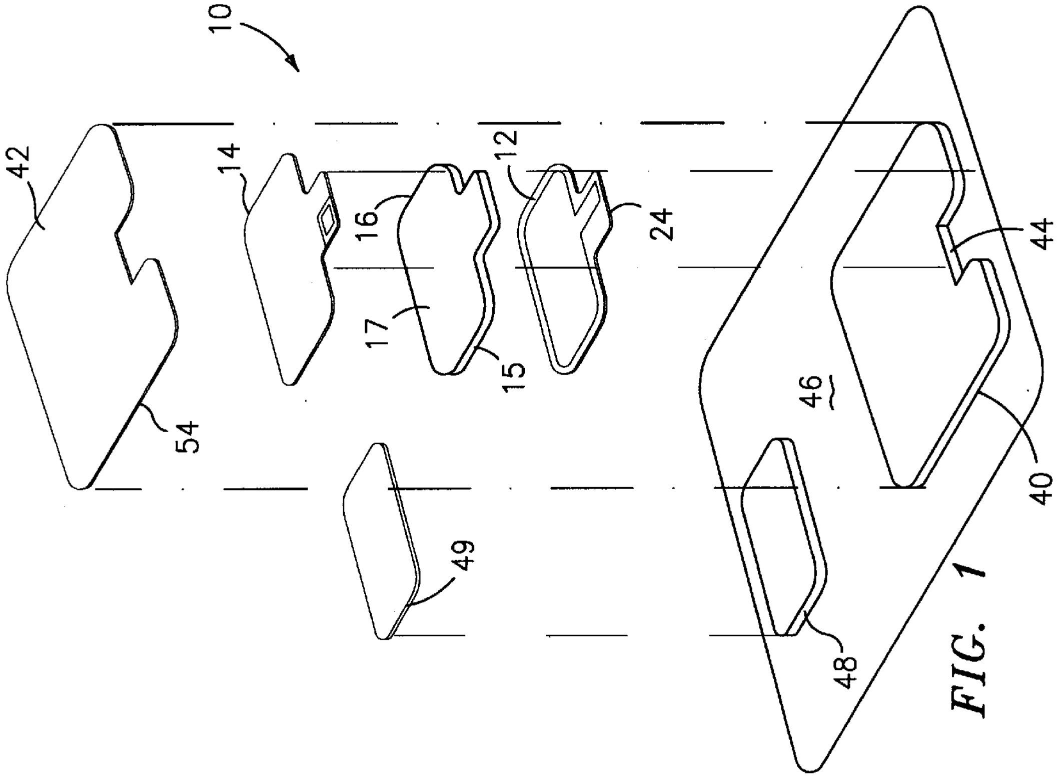
FIG. 1 is an exploded view of an acoustic sensor in accordance with the present invention.

Referring now to the drawings, FIG. 1 illustrates the acoustic sensor 10 of the present invention. The electromechanically active portion of the sensor 10 comprises first and second sensor elements 12 and 14 respectively and substrate 16. Each of the sensor elements 12 and 14 is preferably formed from a low cost, thin piezoelectric polymer material which is monoaxial and has a thickness in the range of from about 20 to about 60 microns. Thin material is desirable because it allows for a smaller area for the sensor and results in cost savings. Experimentation has shown that for good high frequency response, the piezoelectric polymer material forming each sensor element should preferably have a thickness of about 25 microns. The surface area dimensions should be less than about 1.5 inch by 1.0 inch. A preferred material for the sensor elements 12 and 14 is monoaxial polyvinyldiflouride.

The piezoelectric polymer material used to form the sensor elements 12 and 14 is preferably "poled" by stretching the material and then subjecting it to a very high electric field that is normal to the plane of the polymer material. The resultant material becomes highly anisotropic. For convenience sake, the axis along which the material is stretched is called the stretch or "1" axis. The "2" axis is in the plane of the polymer sheet material forming the sensor element and containing the "1" axis but normal to the "1" axis. The "3" axis is perpendicular to the plane of the polymer sheet material and parallel to the electrical field that is applied. The piezoelectric polymer material causes equal but opposite electrical charges to occur on the surfaces of the material when forces are applied to it. Equal and opposite forces applied to the edges of the polymer material and parallel to the "1" axis cause far larger electric charges to appear on the surface than when the same forces are applied parallel to the "2" or "3" axes. Therefore, the polymer material forming the sensor elements 12 and 14 is oriented to maximize the electrical signal(s) produced by the sensor.

As previously mentioned, the sensor elements 12 and 14 create electrical signals in response to mechanical flexure. When the sensor 10 is flexed, the state of tension in each respective sensor element 12, 14 changes in opposite ways. For example, if the tension in sensor element 12 is increasing, the tension in sensor element 14 is simultaneously decreasing. Due to the piezoelectric nature of the sensor elements 12 and 14, electrical signals are generated by the sensor elements; however, they are of opposite polarity. The sensor 10 is used with a connector that completes the circuit of the sensor by joining a conducting area of the sensor element 12 with a conducting area of sensor 14 and a grounded Faraday shield that envelops the connector, the signal carrying wires, and the high impedance portion of the electronic amplification circuit. The sensor 10, when connected to a measuring device (not shown) requires a differential amplifier (not shown) that algebraically subtracts the signal of one sensor-element from that of the other sensor element, thereby effectively adding the magnitudes of the two signals. Airborne acoustic energy that is incident on the sensor 10 causes simultaneously increasing or decreasing compression across the thickness of both sensor elements 12 and 14 so that the signals generated in response are of the same polarity. These unwanted signals are subtracted by the differential amplifier to produce little or no resultant signal. Therefore, the acoustic sensor 10 of the present invention, when used with a differential amplifier, rejects unwanted airborne acoustic noise.

As shown in FIG. 1, the two sensor elements 12 and 14 are separated by a substrate formed by one or more layers 16 of a flexible, elastomeric material. The material selected for the substrate layer(s) 16 should be one that offers little resistance to flexure. The piezoelectric polymer material forming the sensor elements 12 and 14 has a relatively high modulus of elasticity, and thus significantly stiffens the acoustic sensor 10 once the sensor elements 12 and 14 are laminated to the opposed surfaces 15 and 17 of the substrate 16. Preferably, the material forming the substrate 16 has a high strength, pressure sensitive adhesive pre-applied to the surfaces 15 and 17. Depending on the other dimensions of the sensor, and the desired frequency emphasis, the thickness of the substrate may vary from about 0.015 inches to about 0.06 inches.

If desired, the substrate 16 could be a laminate of two layers of a flexible and elastic material bonded to either side of a flexible but inelastic sheet of material, such as copper foil or polyester.

Figure 2:
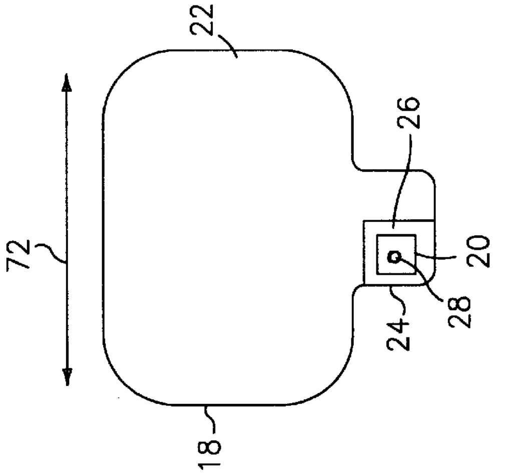
FIG. 2 illustrates the first surface of the acoustic sensor of FIG. 1 and the electrically conductive areas thereon.

The two sensor elements 12 and 14 are preferably identical in design and configuration. Each sensor element has a substantially rectangular main portion and an adjoining connecting tab portion 24. As shown in FIG. 2, the outer surface 18 of each sensor element contains two electrically conductive areas 20 and 22. The first electrically conductive area 20 is small and covers somewhat less than half of the connecting tab portion 24 of the sensor element. The other electrically conductive area 22 covers the remainder of the surface 18 except for a small border 26 around the area 20, which border serves to electrically isolate the two areas 20 and 22. The electrically conductive area 20 and 22 are preferably formed by an elastomeric, electrically conductive ink, such as silver ink, which has been silk screened on the surface 18.

In a preferred embodiment of the present invention, the area 20 is in contact with a hole 28 which passes through the sensor element from the outer surface 18 to the inner surface 30. The hole 28 has its surfaces coated with an electrically conductive material such as an electrically conductive ink so as to form an electrical connection between the electrically conductive area 20 and an electrically conductive area 32 on the inner surface 30.

If desired, the electrically conductive area 22 may be partially coated by a very thin layer of elastomeric material for cosmetic purposes.

Figure 3:
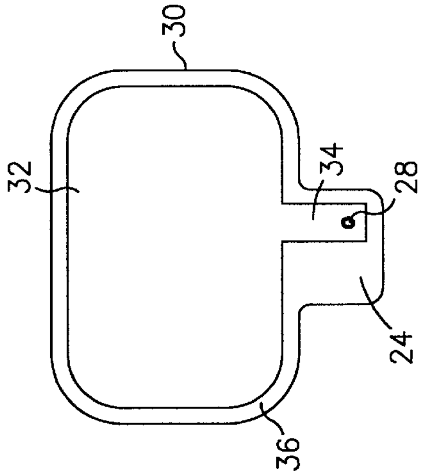
FIG. 3 illustrates the second surface of the acoustic sensor of FIG. 1.

As shown in FIG. 3, the inner surface 30 of each sensor element contains only the electrically conductive area 32, which area includes a narrowing conducting run 34 which connects the area 32 to the plated hole 28. In this way, the area 32 is electrically connected to the area 20. The area 32 is also formed by silk screening an electrically conductive ink on the surface 30. A perimeter margin 36 having no electrically conductive ink thereon surrounds the area 32.

Referring now to FIG. 1, the inner surfaces 30 of the sensor elements 12 and 14 are bonded to the surfaces 15 and 17 of the substrate 16 to form the active portion of the sensor 10. A layer 40 of hydrogel or medical grade adhesive is bonded to outer surface 18 of the sensor element 12 and an optional cover layer 42, preferably of low density polyethylene, is bonded to the outer surface 18 of the sensor element 14 and surrounding portions of the hydrogel or medical grade adhesive that can optionally extend beyond the active sensor 10. The layer 40 is provided for adhesion to the subject and for aiding the packaging of the sensor by adhering, not very aggressively to the plastic liner card or support layer 46. The hydrogel layer 40 must not contact the connector tab portion 24 of sensor 10. One way to do this is for the hydrogel layer 40 to have a notched portion 44 so that when the active portion of the sensor 10 is positioned on the hydrogel layer 40, the connecting tab portion 24 of the sensor element 12 has no hydrogel beneath it. This allows the connecting tab portion 24 of the sensor element 12 to remain free for easy mating with a connector. Alternatively, the sensor 10 could be mounted on a basically rectangular piece of hydrogel with the connector tab portion 24 of the sensor 10 protruding from the hydrogel so that there is no hydrogel under the connector tab portion 24.

The optional layer 42 has substantially the same dimensions and shape as the layer 40 so that the connecting tab portion 24 on sensor element 14 remains free for easy mating with a connector. The layer 42 preferably has a thickness in the range of from about 0.001 to about 0.002 inches of polyethylene or from about 0.015" to about 0.032" of soft foam tape. The purpose of the optional cover layer 42 is to ensure that the active portion of the sensor 10 remains in intimate contact with the layer 40 and to prevent the hydrogel or any other adhesive material from sticking to any packaging material. The cover layer 42 is preferably affixed to the sensor element 14 by a pressure sensitive adhesive on the inner surface 54 of the cover layer.

Preferably, the sensor 10 is laminated to a support layer 46, such as a plastic liner card, for packaging purposes. As shown in FIG. 1, the liner card is affixed to a surface of the hydrogel layer 40. The plastic liner card 46 is preferably formed from a release liner material that allows a user to easily lift the sensor 10 off.

The liner card 46 plays no role in the functionality of the sensor. It is merely provided for packaging purposes. Several cards, perhaps as many as ten, may be joined along an edge, and highly perforated or partially sliced to facilitate accordion-like folding along those edges for packaging and storage.

If desired, a separate piece 48 of hydrogel may be affixed to the liner card 46 so that a user can separate it from the card 46 and use it as needed. The hydrogel piece 48 should be covered with a layer of polyethylene 49 or other suitable material to facilitate packaging and use.

Prior to use, the acoustic sensor is mated with a connector with a signal wire leading to an amplifier (not shown). In prior art devices, the axis of the connector and the wire that gets connected to the sensor is parallel to the stretch axis of the material. Because of this, physical vibrations travelling along the wire to those sensors created high levels of unwanted electrical noise output from the sensor. When the acoustic sensor 10 of the present invention is used, the axis of the connector 60 and the wire(s) 70 is preferably perpendicular to the stretch axis 72 of the sensor elements so that the electrical noise generated within the sensor 10 due to wire-borne vibrations is dramatically reduced.

Figure 4:
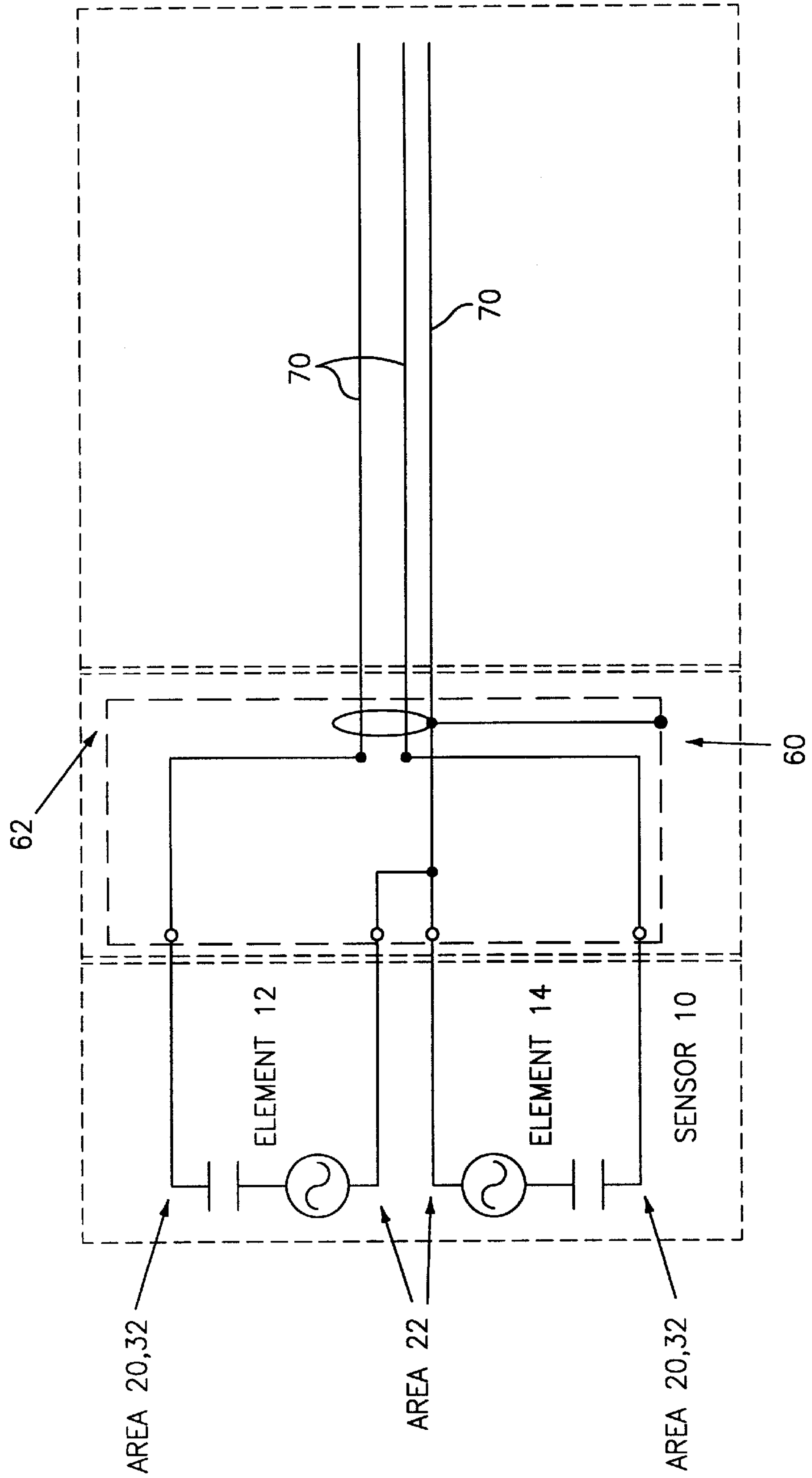
FIG. 4 illustrates the functional requirement of a connector to be used with the acoustic sensor of the present invention.

Once the sensor 10 has been assembled and connected to its electronics, as shown in FIG. 4, both conducting surfaces 32 of the sensor elements 12, 14 are electrically joined and connected to a grounded connector shield 62. Together, areas 32 of elements 12, 14 and the connector shield 62 form a Faraday shield that envelops sensor element areas 20 and both signal leads of the wires 70 to minimize pickup of unwanted electromagnetic signals. This enables conducting areas 22 of the two sensor elements 12 and 14 to be electrically disconnected until mated with the sensor connector, thereby eliminating the need for, and the high cost of, attaching connector pins to the sensor. Using disconnected sensor elements also eliminates any need to fold the piezoelectric polymer material of the sensor elements during assembly.

Figure 5:
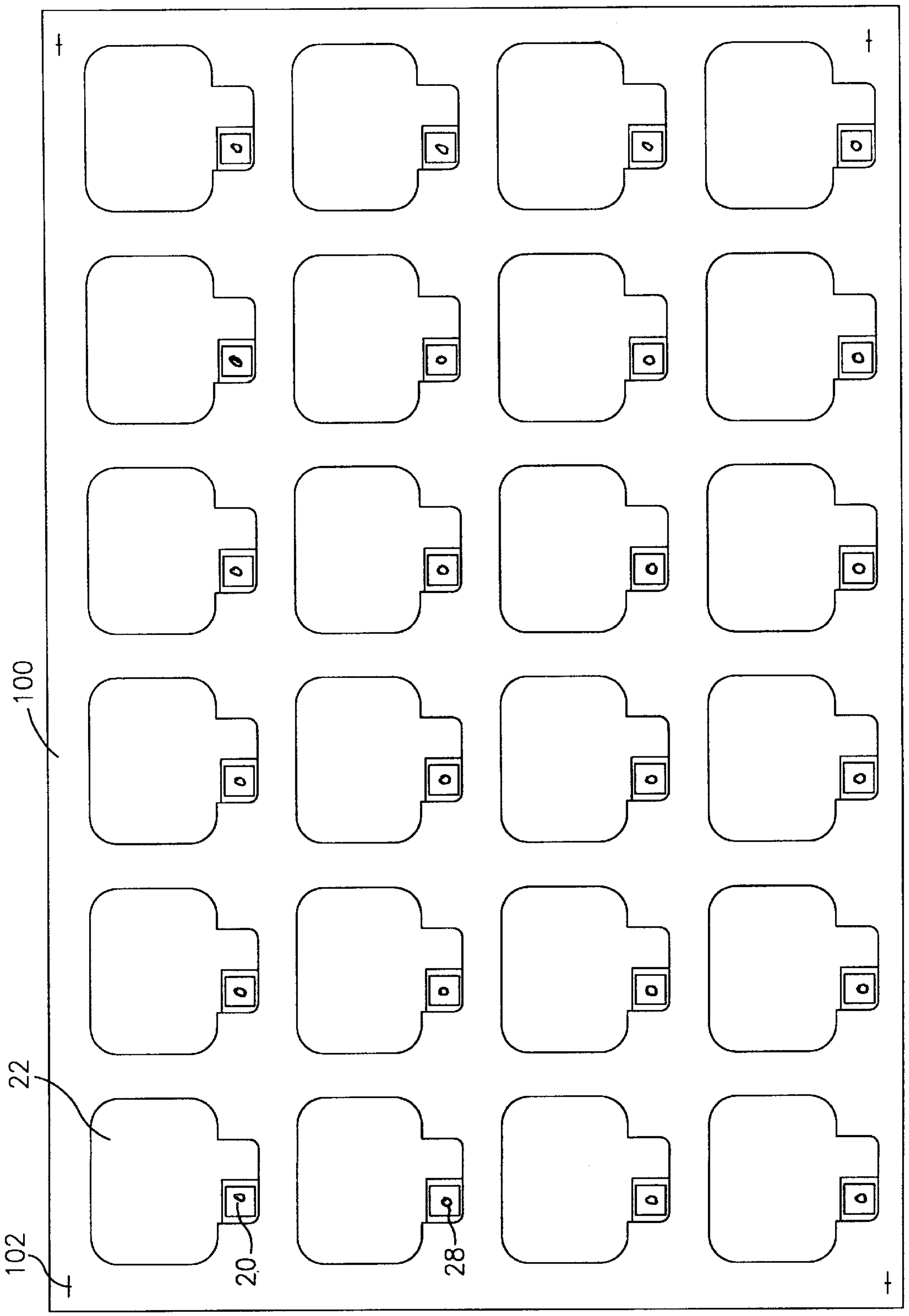
FIGS. 5 and 6 illustrate a sheet of piezoelectric polymer material having sensor elements fabricated thereon.
Figure 6:
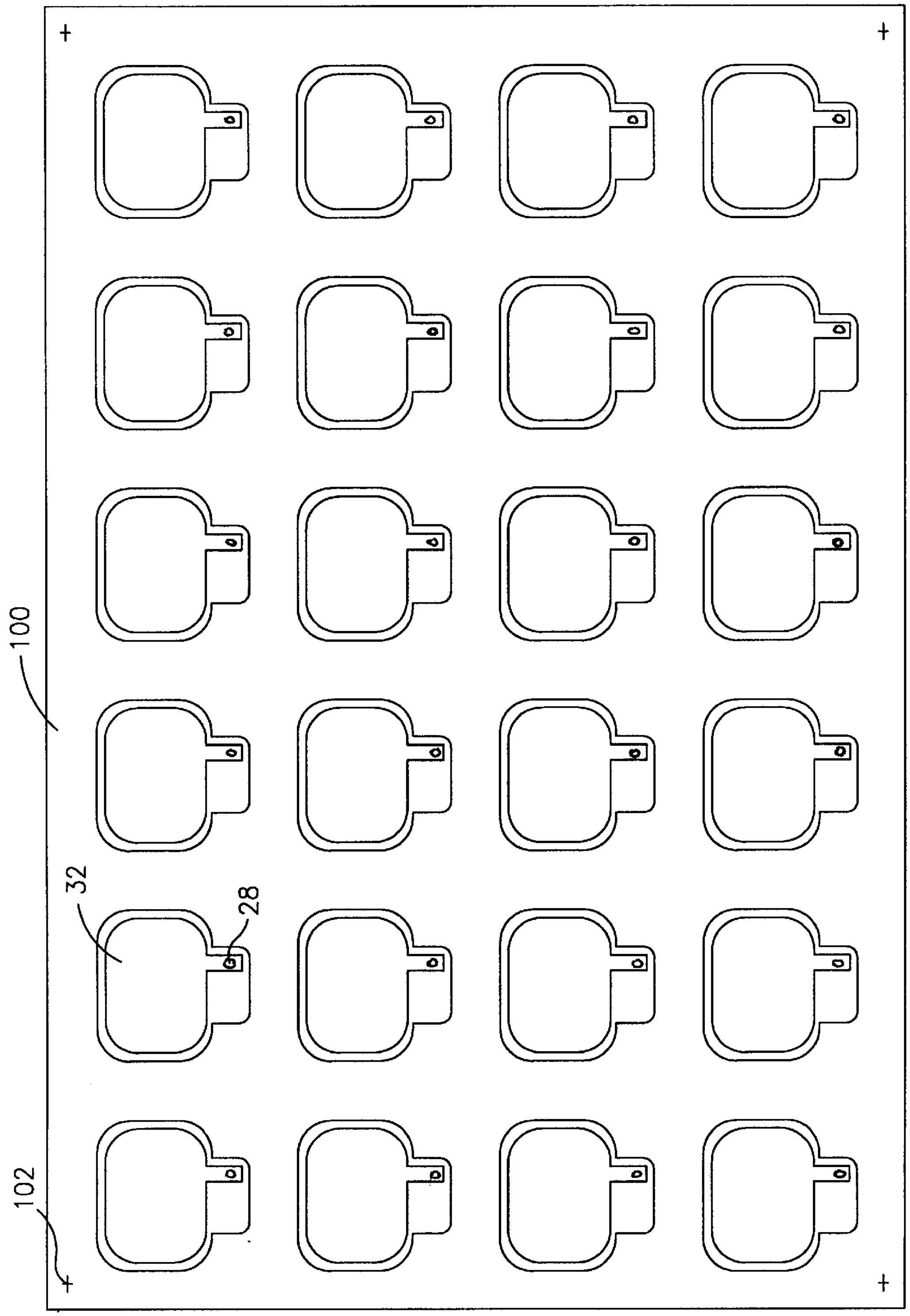

The sensor 10 of the present invention is preferably fabricated in the following manner:

As shown in FIGS. 5 and 6, sheet stock 100 of piezoelectric polymer material that has been poled by standard means is screen printed with silver ink on a first side to form an array of conducting ink patterns that correspond to conducting areas 20, 22 on surface 18 of numerous elements 12. The separations of the individual element patterns is regular and all inter-element spacing is identical. Also, screen printed onto the sheet stock are registration marks 102 to facilitate registration of the sheet stock during subsequent screen printing and lamination processes. The registration marks are visible from both sides because the unprinted sheet stock is transparent. A second screen printing operation on the same side of the same sheet is then used to apply a conformal coating over the elements. The sheet stock 100 is then turned over, tiny holes are punched or die cut in the right locations for the plated (conducting) holes 28, and the conducting areas 32 of surfaces 30 are screen printed onto the sheet stock. This process electrically joins areas 20 and 32. The entire process is repeated to form an identical array of numerous elements 14 on a second sheet of piezoelectric polymer stock. Next, the sheets bearing elements 12 are laminated to a sheet of the substrate 16 material so that surfaces 30 of the array of elements 12 is bonded to surface 17 of the substrate material sheet stock. Then, the piezoelectric polymer sheet bearing elements 14 are laminated to the partial assembly so that surfaces 30 of elements 14 are bonded to surface 15 of the substrate sheet stock. Prior to this lamination, care and appropriate fixturing must be used to ensure proper registration of elements 12 with elements 14 after the bonding operation is complete. The final step in this part of the assembly process is to die cut the entire laminate sheet into individual sensor subassemblies. These are the active portions of the completed sensors.

After the active portion of the sensor 10 has been assembled, the sensor 10 is laminated to a plastic liner card 46 having a layer 40 of hydrogel affixed thereto. The hydrogel layer 40 may be die cut and is self-adhered to the plastic liner card. Thereafter, an optional cover layer 42, preferably of low density polyethylene, is affixed or laminated to the outer surface 18 of the sensor element 14 by a pressure sensitive adhesive on the surface 54 of the polyethylene layer. If desired, this lamination phase may be automated so as to drastically reduce labor costs.

The present design greatly enhances convenience by mounting the active sensor portion on hydrogel and covering the assembly with a thin layer of low density polyethylene or alternatively soft foam tape so that only the surface to be adhered to the subject has exposed adhesive. If desired, adhesive tape or hydrogel 48 may be supplied with the sensor 10 on the plastic card liner 46.

While it is preferred that the cover layer 42 be formed from a low density polyethylene material, it should be recognized that the cover layer 42 could be formed from any suitable material which is easily stretched in comparison to the piezoelectric polymer material forming the sensor elements 12 and 14. The cover layer 42 may also be omitted.

The hydrogel that is provided with the sensor 10 can be repositioned several times without significant loss of adhesion to the skin or other surfaces. However, in situations where the sensor 10 need not be repositioned, less expensive methods of adhesion are possible. For example, double-sided medical adhesive tape could be used between the sensor 10 and the mounting surface to adhere the sensor to the sound containing material of interest. It is also possible to substitute a viscous paste similar to toothpaste for the adhesion mechanism. In such an application, the paste would be smeared on the area and the active portion of the sensor would be pushed into it whereupon it becomes mechanically and acoustically coupled to the material of interest.

While the sensor 10 has been described as having a plated through hole as forming an electrical connection between the electrically conductive areas 20 and 32, it should be recognized that other types of electrical connections could be used. For example, the electrical connection could be formed by small metal spikes or pins that are part of the connector, which spikes or pins pierce through the sensor elements at the location of the plated through hole 28. The electrical contact is then formed because areas 20 and 22 of each sensor element both contact the spikes or pins.

The acoustic sensor of the present invention has many potential applications. For medical purposes, the sensor can be used to monitor any acoustic energy generated within the body. Examples include heart sounds, breath sounds, snoring sounds, Korotkoff sounds, bowel sounds, and the rushing sound of blood passing by obstructions in the arteries. Utility has been demonstrated in emergency medical situations for taking accurate, auscultated blood pressure measurements in very high noise environments. The sensor can likewise be used to continuously monitor blood pressure during a stress test without the patient having to stop exercising. In pest control, the sensor can be used to detect the sounds associated with the destructive activity of insects and rodents. For intrusion detection, the sensors can be buried below ground to detect approaching foot steps. When properly mounted on pipes, the sensor will detect the sound of gasses or liquids flowing through valves.

It is apparent that there has been provided in accordance with this invention a low-cost, disposable, polymer-based, differential output flexure sensor and a method of fabricating same which fully satisfy the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications and variations as fall within the spirit and the broad scope of the appended claims.

What is claimed is:

1. A sensor comprising:

an active portion which includes a first sensor element, a second sensor element, and a substrate positioned between said first and second sensor element;

each said sensor element being formed from a piezoelectric polymer material having a main portion and a connecting tab portion adjacent one side of said main portion, said connecting tab portion being narrower than said one side of said main portion;

each said sensor element having a first electrically conductive area on a first surface of said tab portion;

each said sensor element further having a second electrically conductive area on a first surface of said main portion, which second electrically conductive area has a portion which extends onto said first surface of said tab portion and is electrically insulated from said first electrically conductive area;

each said sensor element further having a third electrically conductive area on a second surface of said main portion, which third electrically conductive area has a portion which extends onto a second surface of said tab portion; and each said sensor element further having means for electrically connecting said first and third electrically conductive areas, said electrical connection means extending through said tab portion.

2. The sensor of claim 1 wherein:

said electrical connection means comprises a hole plated with an electrically conductive material.

3. The sensor of claim 2 wherein:

each of said electrically conductive areas being formed from an electrically conductive ink which has been applied to said piezoelectric polymer material; and said electrically conductive material for plating said hole comprises said electrically conductive ink.

4. The sensor of claim 2 wherein:

said electrical connection means comprises at least one spike that pierces through said tab portion, said at least one spike being formed from an electrically conductive material.

5. A sensor comprising:

an active portion which includes a first sensor element, a second sensor element, and an intermediate substrate;

each said sensor element being formed from a piezoelectric material having a main portion and an adjoining connector tab portion;

each said sensor element having a first surface with a first electrically conductive area substantially covering said first surface and having a first conductive portion which extends onto an adjoining first surface of said tab portion;

each sensor element further having a second electrically conductive area on said first surface of said tab portion, said second electrically conductive area being electrically insulated from said first electrically conductive area;

each sensor element further having a second surface with a third electrically conductive area substantially covering said second surface and having a second conductive portion which extends onto an adjoining second surface of said tab portion; and each said sensor element having the same one of said first and second surfaces joined to said substrate.

6. The sensor of claim 5 wherein said active portion further includes a substrate positioned between said first and second sensor elements, said substrate being formed by at least one layer of a flexible material.

7. The sensor of claim 6 wherein:

said substrate has opposed surfaces with a pressure sensitive adhesive material thereon; and said second surfaces of said first and second sensor elements are affixed to said opposed surfaces of said substrate by said pressure sensitive adhesive material.

8. The sensor of claim 5 further comprising:

a layer of hydrogel affixed to a first one of said first and second sensor elements; and said hydrogel layer having a notched portion so that said connecting tab portion on said first one of said first and second sensor elements has no hydrogel beneath it.

9. The sensor of claim 8 further comprising:

a cover layer affixed to a second one of said sensor elements, said cover layer being configured so that said connecting tab portion on said second sensor element has no portion of said cover layer over it.

10. The sensor of claim 9 wherein said cover layer is formed from a low density polyethylene material or a soft foam tape.

11. The sensor of claim 9 further comprising:

said sensor being laminated to a support layer to facilitate packaging of said sensor.

12. The sensor of claim 11 wherein said support layer comprises a plastic card composed of a release liner material to allow the sensor to be removed therefrom.

13. A sensor according to claim 5 wherein said second surface of each of said sensor elements is mated to a surface of said substrate.

14. A sensor comprising:

an active portion comprising a first sensor element, a second sensor element, and a substrate material positioned between said first and second sensor elements;

each said sensor element being formed from a piezoelectric polymer material having a main portion and a connecting tab portion, said tab portion being narrower than said main portion;

each said sensor element having electrically conductive areas on a first surface of said main portion and said connecting tab portion and on a second surface of said main portion and said connecting tab portion;

at least one wire extending along a first axis;

means for connecting said at least one wire to said sensor elements; and said piezoelectric polymer material forming each of said first and second sensor elements having a stretch axis substantially perpendicular to said first axis for reducing unwanted noise caused by mechanical vibrations carried by the at least one wire.

15. A sensor according to claim 14 wherein said sensor element has:

a first electrically conductive area on a first surface of said main portion which extends onto an adjoining first surface of said tab portion;

a second electrically conductive area on said first surface of said tab portion electrically isolated from said first electrically conductive area; and a third electrically conductive area on a second surface of said main portion opposed to said first surface, said third electrically conductive area having a portion which extends onto an adjoining second surface of said tab portion.

16. A sensor of claim 15 wherein said second and third electrically conductive areas are electrically connected together.

17. A sensor element for use in an acoustic sensor comprising:

means for sensing acoustic energy;

said sensing means including a main portion and a connecting tab portion adjacent one side of said main portion;

a first electrically conductive area on a first surface of said connecting tab portion;

a second electrically conductive area covering substantially all of a first surface of said main portion and extending on to said first surface of said tab portion;

said first and second electrically conductive areas being separated from each other; and a third electrically conductive area on a second surface of said main portion, said third electrically conductive area further covering a portion of a second surface of said tab portion, wherein said first and third electrically conductive areas are electrically connected.

18. The sensor element of claim 17 wherein said first electrically conductive area covers less than half of the first surface of said tab portion.

19. The sensor element of claim 17 wherein said main portion is substantially rectangularly shaped and said tab portion is narrower than said one side.

20. The sensor element of claim 17 wherein each of said conductive areas is formed from an electrically conductive ink.

* * * * *